United States Patent [19]

Giesler et al.

[11] Patent Number: 5,702,383
[45] Date of Patent: Dec. 30, 1997

[54] BLOOD COMPONENT COLLECTION SYSTEMS AND METHODS USING AN INTEGRAL SAMPLING DEVICE

[75] Inventors: Richard Giesler, Deerfield; Ulrich C. Geissler, Barrington Hills; Margaret E. Stanford, Winnetka, all of Ill.; William E. Johnson, Gainsville, Mo.

[73] Assignee: Baxter International Inc., Deerfield, Ill.

[21] Appl. No.: 664,806

[22] Filed: Jun. 17, 1996

Related U.S. Application Data

[62] Division of Ser. No. 269,932, Jul. 1, 1994, abandoned.

[51] Int. Cl.⁶ ................................................. A61B 19/00
[52] U.S. Cl. ........................ 604/409; 604/403; 128/898
[58] Field of Search ........................................ 604/403, 408, 604/409, 410, 903; 128/DIG. 24, 898

[56] References Cited

U.S. PATENT DOCUMENTS

| | | | |
|---|---|---|---|
| 2,661,743 | 12/1953 | Archer | 604/403 |
| 2,950,716 | 8/1960 | Bellamy, Jr. et al. | 604/409 |
| 3,654,924 | 4/1972 | Wilson et al. | |
| 4,250,893 | 2/1981 | White | |
| 4,786,286 | 11/1988 | Cerny et al. | 604/403 |
| 4,902,287 | 2/1990 | Carmen et al. | 604/403 |
| 4,994,057 | 2/1991 | Carmen et al. | 604/403 |
| 5,074,839 | 12/1991 | Choksi et al. | |
| 5,078,970 | 1/1992 | Teodorescu et al. | |
| 5,132,026 | 7/1992 | Baluyot et al. | |

Primary Examiner—John G. Weiss
Assistant Examiner—Dennis Ruhl
Attorney, Agent, or Firm—Daniel D. Ryan; Denise M. Serewicz; Bradford R. L. Price

[57] ABSTRACT

A squeezable, resilient pouch is used for collecting a blood sample. The walls of the pouch are moved together in response to the application of an external squeezing force. The squeezing force collapses the pouch and expels fluid from it. Upon removal of the squeezing force, the resilience of the pouch walls moves them apart. The resilient expansion of the pouch creates suction that draws a fluid sample into the pouch. The pouch can be attached to a blood collection and/or storage container by flexible tubing in a way that prevents communication with the atmosphere. By squeezing the pouch, the user obtain a sample of the blood without using special tools and with no danger of activating or damaging the blood component being sampled.

5 Claims, 2 Drawing Sheets

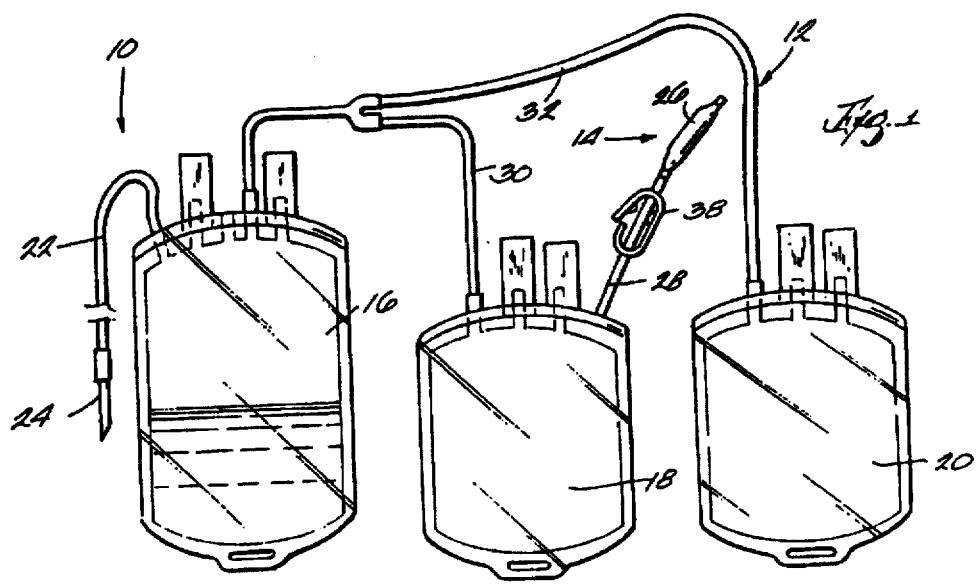
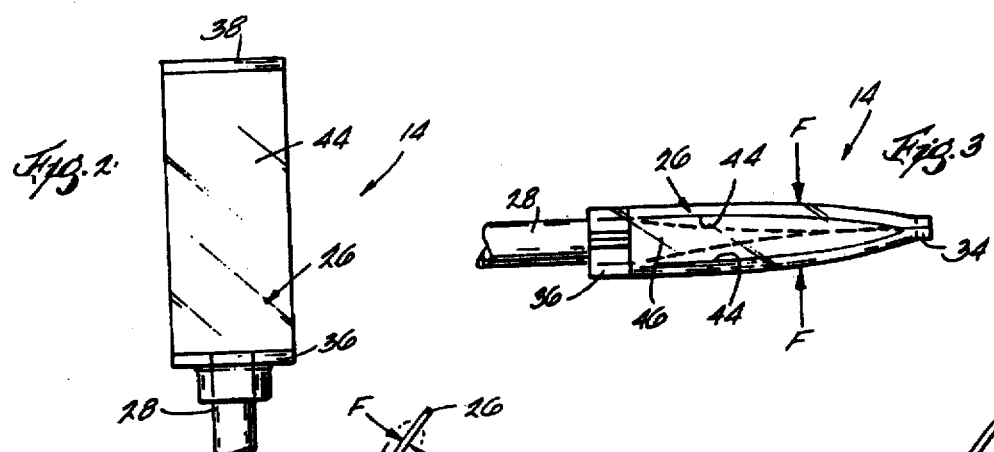
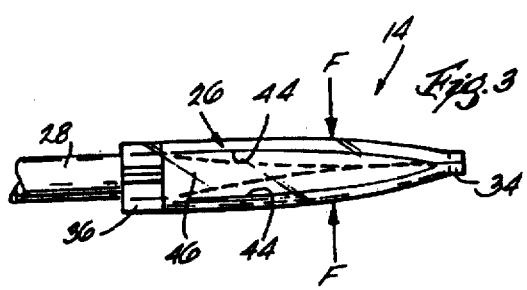
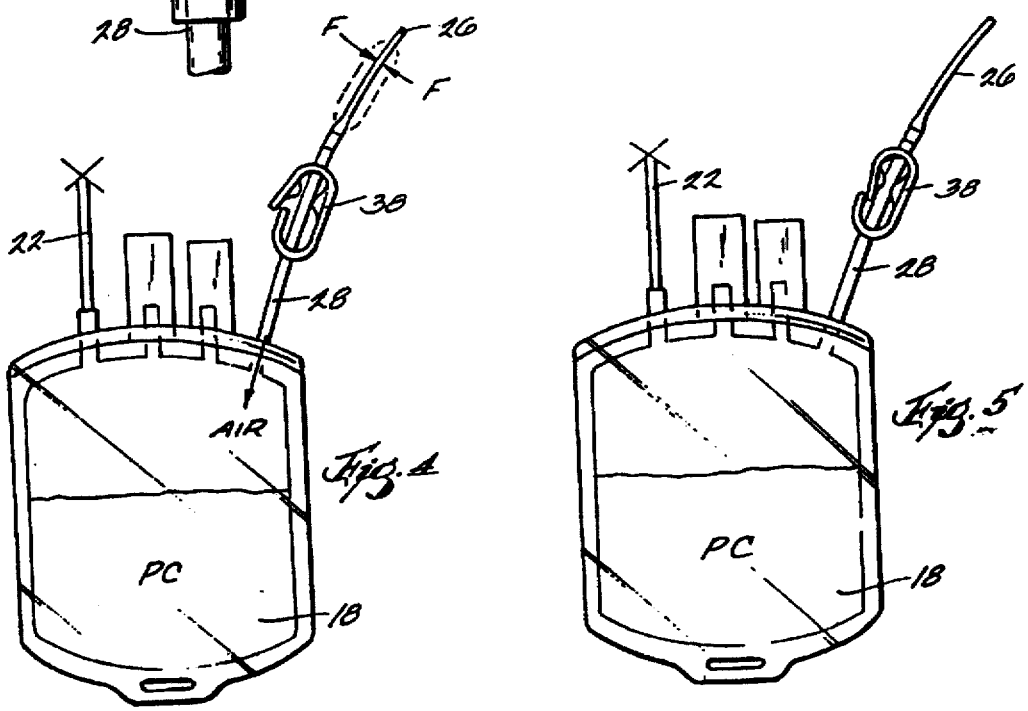
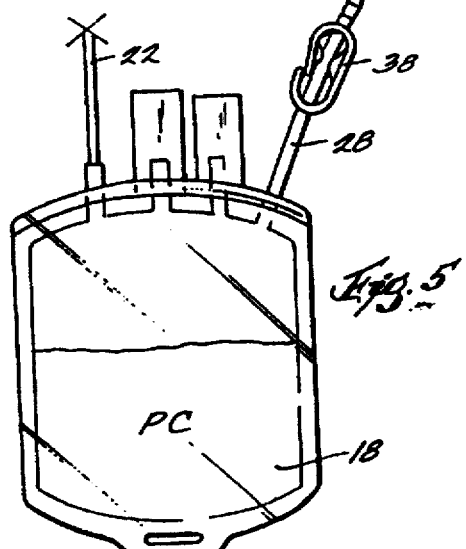

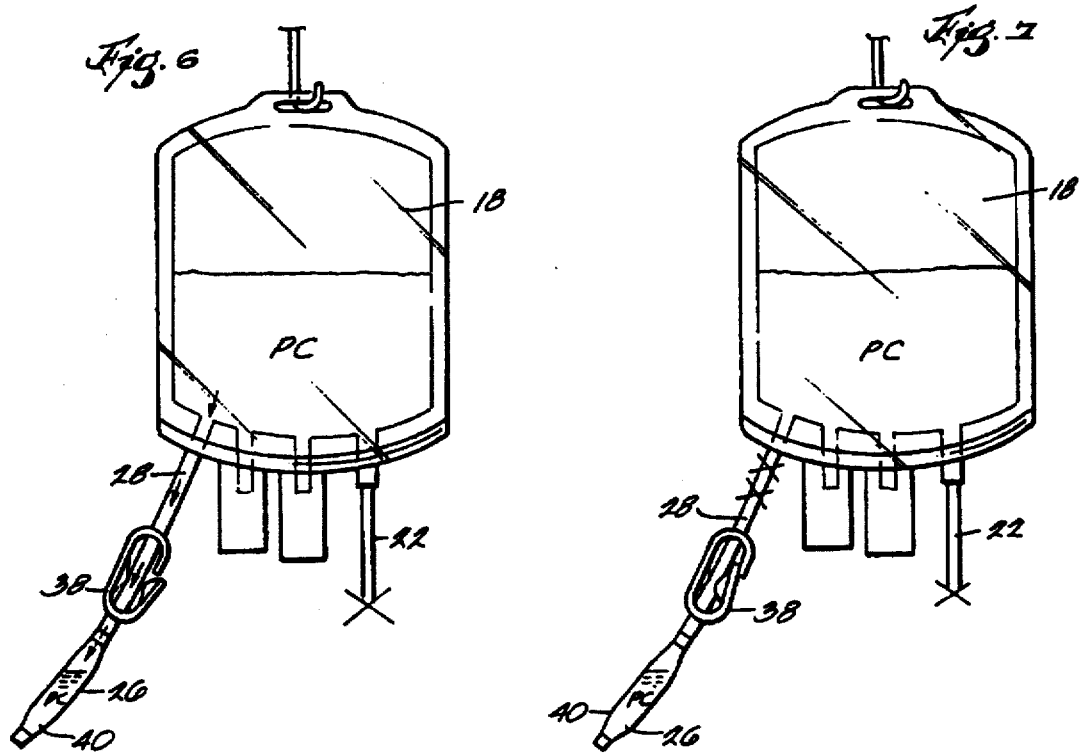
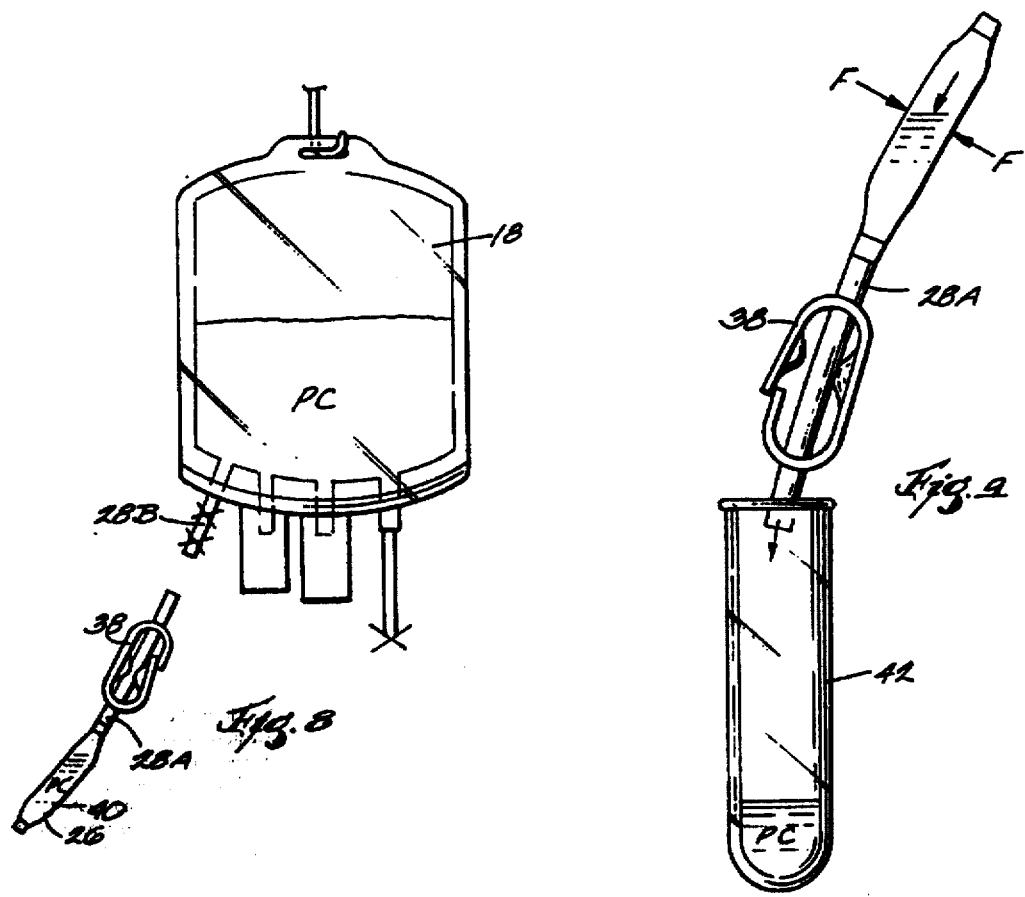

BLOOD COMPONENT COLLECTION SYSTEMS AND METHODS USING AN INTEGRAL SAMPLING DEVICE

This is a divisional of application Ser. No. 08/269,932 filed on Jul. 1, 1994, now abandoned.

FIELD OF THE INVENTION

The invention generally relates to blood collection and processing systems and methods.

BACKGROUND OF THE INVENTION

Most of the whole blood collected from donors today is not itself stored and used for transfusion. Instead, the whole blood is separated into its clinically proven components (typically red blood cells, platelets, and plasma), which are themselves individually stored and used to treat a multiplicity of specific conditions and diseased states. For example, the red blood cell component is used to treat anemia; the concentrated platelet component is used to control thrombocytopenic bleeding; and the platelet-poor plasma component is used as a volume expander or as a source of Clotting Factor VIII for the treatment of hemophilia.

Systems composed of multiple, interconnected plastic bags have met widespread use and acceptance in the collection, processing and storage of these blood components. In the United States, these multiple blood bag systems are subject to regulation by the government. For example, the plastic materials from which the bags and tubing are made must be approved by the government. In addition, the maximum storage periods for the blood components collected in these systems are prescribed by regulation.

In the United States, whole blood components collected in a nonsterile, or "open", system (i.e. one that is open to communication with the atmosphere) must, under governmental regulations, be transfused within twenty-four hours. However, when whole blood components are collected in a sterile, or "closed", system (i.e., one that is closed to communication with the atmosphere), the red blood cells can be stored up to forty-two days (depending upon the type of anticoagulant and storage medium used); the platelet concentrate can be stored up to five days (depending upon the type of storage container); and the platelet-poor plasma may be frozen and stored for even longer periods. Conventional systems of multiple, interconnected plastic bags have met with widespread acceptance, because these systems can reliably provide the desired sterile, "closed" environment for blood collection and processing, thereby assuring the maximum available storage periods.

Before transfusing cellular blood components it is important assure that the blood type of the recipient matches the blood type of the donor. For this reason, conventional blood collection procedures collect small aliquots or samples of the donated cellular blood components for use in crossmatching and typing the donor's blood prior to transfusion.

Typically, the samples are obtained by expressing a small amount of the collected component from the collection bag back into the integrally attached tubing serving the bag. In this process, one or more sealed pockets are formed along the length of the tubing using a conventional heat sealing device (for example, the Hematron® dielectric sealer sold by Baxter Healthcare Corporation). The pockets retain the samples for analysis.

These conventional techniques for collecting samples typically require special tools and added manipulation. For example, before expressing samples into the tubing, a tube stripper is often used to clear the tubing of other blood components that could contaminate the sample. Later, a syringe is often used to transfer the samples from the pockets to a test tube for analysis.

A need still exists for further improved systems and methods for processing blood components for transfusion or storage in a way that lends itself to use in closed multiple blood bag system environments and that assures accurate crossmatching and typing of cellular blood components prior to transfusion without the need for special tools or extra manipulation.

SUMMARY OF THE INVENTION

The invention provides methods and systems for collecting a blood sample from a collection and/or storage container without using special tools and manipulation.

The systems and methods that embody the features of the invention include a squeezable, resilient pouch for collecting a blood sample. The walls of the pouch are moved together in response to the application of an external squeezing force. The squeezing force collapses the pouch and expels fluid from it. Upon removal of the squeezing force, the resilience of the pouch walls moves them apart. The resilient expansion of the pouch creates suction that draws a fluid sample into the pouch.

The pouch can be attached to a blood collection and/or storage container by flexible tubing in a way that prevents communication with the atmosphere. Merely by squeezing the pouch, the user draws (and later expels) a sample of the blood for analysis without using special tools and with no danger of activating or damaging the blood component being sampled.

Other features and advantages of the invention will become apparent upon review of the following description, drawings, and appended claims.

BRIEF DESCRIPTION OF THE DRAWINGS

FIG. 1 is a largely view of a blood collection system that includes a sampling device that embody the features of the invention;

FIG. 2 is an enlarged top view of the sampling device shown in FIG. 1;

FIG. 3 is an enlarged side view of the sampling device shown in FIG. 2;

FIG. 4 is a largely schematic view of readying the sampling device for use by evacuating air from it;

FIG. 5 is a largely schematic view of the sampling device when ready for receiving a component sample;

FIG. 6 is a largely schematic view of drawing the component sample from the associated component storage bag into the sampling device;

FIG. 7 is a largely schematic view of preparing the sampling device, now containing a component sample, from the associated component storage bag;

FIG. 8 is a largely schematic view of the sampling device, now containing a component sample, separated from the associated component storage bag; and FIG. 9 is a largely schematic view of expressing the component sample from the sampling device into the sampling chamber for analysis.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

A blood collection system 10 is shown in FIG. 1. The system 10 comprises a blood collection and processing assembly 12 comprises a multiple blood bag system. According to the invention, the system 10 includes at least one integral sampling device 14, which FIGS. 2 and 3 show in greater detail.

The assembly 12 has a primary bag or container 16 and one or more integrally attached transfer bags or containers 18 and 20. In use, the primary bag 16 (which is typically also called a donor bag) receives whole blood from a donor through integrally attached donor tubing 22 by means of a phlebotomy needle 24. A suitable anticoagulant is contained in the primary bag 16.

The transfer bags 18 and 20 are attached to the primary bag 16 by integrally attached transfer tubing 30 and 32. The transfer bags 18 and 20 are intended to receive the platelet and plasma blood components for processing. The first transfer bag 18 ultimately serves as the storage container for the platelet concentrate, and the second transfer bag 20 ultimately serves as the storage container for the platelet-poor plasma.

All of the bags 16, 18, and 20 and tubing 22, 30, and 32 associated with the processing assembly 12 can be made from conventional approved medical grade plastic materials, such as polyvinyl chloride plasticized with di-2-ethylhexylphthalate (DEHP). Alternatively, the first transfer container 18, which is intended to store the platelet concentrate, can be made of polyolefin material (as disclosed in Gajewski et al U.S. Pat. No. 4,140,162) or a polyvinyl chloride material plasticized with tri-2-ethylhexyl trimellitate (TEHTH). These materials, when compared to DEHP-plasticized polyvinyl chloride materials, have greater gas permeability that is beneficial for platelet storage.

In the illustrated and preferred embodiment (see FIGS. 2 and 3), the sampling device 14 is includes a plastic pouch 26 formed from flexible, resilient PVC, either in sheet or tubular form. In the illustrated and preferred embodiment, the pouch 26 is formed from a length of PVC tubing heat sealed at its opposite ends 34 and 36. Flexible PVC tubing 28 is integrally connected at one end to the pouch 26 and at the other end to the bag 18.

The resilience of the pouch walls 44 permits moving them together in response to the application of an external squeezing force by the user (which is identified by arrows and the letter F in FIGS. 3, 4, and 9). The user exerts this squeezing force while holding the pouch 26 between his/her thumb and forefinger. The squeezing action collapses the pouch 26 to expel fluid from the pouch interior 46 through the tubing 28. Due to their resilience, the walls 44 move back apart when the squeezing force is removed. As the pouch walls 46 separate, they create a vacuum that draws or sucks fluid into the pouch interior 46 through the tubing 28, much like an eye dropper.

The tubing 28 preferably carries a conventional in-line manual clamp 38, such as a so-called Roberts clamp or a conventional slide clamp. The clamp 38 opens and closes flow communication in the flexible tubing 46 between the pouch 26 and the storage container 18.

The size, and thus the volume, of the pouch 26 can vary, depending upon the size of the sample required by the user. For most blood collection purposes, the pouch 26 encloses a volume of about 2 to 3 mL.

Furthermore, plastic materials other than PVC can also be used in forming the pouch 26, provided that material has the resilience to allow compression and expansion of the pouch 26 during use and, of course, provided that the material is suited for contact with blood.

In an alternative embodiment (not shown), the tubing 28 can comprise a sterile connecting system disclosed, for example, in Spencer U.S. Pat. No. 4,412,835 or Granzow et al U.S. Pat. Nos. 4,157,723 and 4,265,280. In this arrangement, the pouch 26 can comprise an initially separate, sterile subassembly that is later attached to the container 18 using a sterile connection when it is time to collect a component sample.

Either when integrally assembled (as FIG. 1 shows) or when assembled using the sterile connection systems (as just described), the blood collection and storage assembly 12 and associated sampling device 14, once sterilized, constitutes a sterile, "closed" system, as judged by the applicable standards in the United States.

In use, whole blood is collected and then separated into its various therapeutic components within the assembly 12. These therapeutic components are typically red blood cells, plasma, and platelets.

A desired amount of whole blood is collected from the donor in the primary bag 16. The phlebotomy needle 24 is separated from the donor tube 22, while sealing the distal end of the donor tube 22. A conventional heat sealing device (for example, the Hematron® dielectric sealer sold by Baxter Healthcare Corporation) can be used for this purpose. The device forms a hermetic, snap-apart seal at the distal end of the donor tubing 22 (this seal is later schematically shown by an "x" in the drawings).

Usually, a small volume of anticoagulated whole blood is expressed out of the primary bag 16 back into the donor tube 22, which is sealed to form a series of chambers where discrete aliquots, or samples, of the donor's whole blood are retained for later analysis.

The collected whole blood is next centrifugally separated within the primary bag 16 into red blood cells and platelet-rich plasma. A layer of white blood cells forms between the red blood cells and the platelet rich plasma.

The platelet-rich plasma is transferred by conventional techniques into the first transfer bag 18, leaving the red blood cells (and, typically, the layer of white blood cells) in the primary bag 16.

The transfer bags 18 and 20 are detached as a unit using snap apart seals formed by the heat sealing device.

The platelet-rich plasma undergoes subsequent centrifugal separation within the first transfer bag 18 into platelet concentrate and platelet-poor plasma. The platelet-poor plasma is transferred into the second transfer bag 20, leaving the platelet concentrate in the first transfer bag 18. The transfer bags 18 and 20 are then separated by snap-apart seals "x" formed in the tubing 32 for subsequent storage of the collected components.

FIG. 4 shows the first transfer bag 18 containing the platelet concentrate (PC) at this stage of the separation process. As FIG. 4 shows, before storing the PC in the bag 18, the user opens the clamp 38 and squeezes the pouch 26 to flatten it as much as possible. The compression of the pouch 26 forces essentially all residual air within it through the tubing and into the bag 18. While still squeezing pouch 26, the user closes the clamp 38 (see FIG. 5). This maintains the pouch 26 in a collapsed, empty condition, ready to receive a component sample during later handling of the bag 18.

It should be realized that these steps of readying the pouch 26 for receiving a component sample can occur at virtually any time, either during or after storage.

When it is time to collect a PC sample within the pouch 26, the user turns the bag 18 upside down, as FIG. 6 shows, to bring the PC into direct flow communication with the tubing 28. Preferable, the user first gently messages the bag 18 to mix the PC within it.

With the bag 18 oriented in this way, the user opens the clamp 38. The collapsed pouch 26 resiliently expands, drawing by suction PC from the bag 18 into the pouch 26.

The pouch 26 fills with a sample 40 of the PC. The user then closes the clamp 38.

To ready the pouch 26 for separation from the bag 18 (see FIG. 17), the user operates the heat sealing device to form one or more seals "x" in the tubing 28 upstream of the now closed clamp 38. The bag 18 and pouch 26 (now filled with the PC sample 40) can be retained in this condition until it is time to analyze the PC sample 40.

When it is time to analyze the sample 40 (see FIG. 7), the user cuts the tubing 28 between the seals "x" and the clamp 38, which, since filling the pouch 26 with the sample 40, remains closed. The user separates the sample-filled pouch 26 and an attached portion of the tubing 28A from the bag 18. The presence of the closed clamp 38 seals on the tubing portion 28A to assure that the pouch 26 remains closed from communication with the atmosphere. The presence of the seals "x" on the other portion of the tubing 28B assures that the bag 18 likewise remains closed from communication with the atmosphere. The sterile integrity of the PC sample 40 within the pouch 26 and the PC component within the bag 18 remains secure.

Next, the user upends the pouch 26 (see FIG. 7), placing the severed tubing 28A into a sampling chamber 42, which is shown as a test tube. The user opens the clamp 38 and squeezes the pouch 26 to expel the PC sample 40 from the pouch 26 into the test tube 42 for analysis.

The invention provides an air-free pouch 26 integrally attached close to a blood collection or storage container. The closeness of the pouch 26 assures a uniform component sample. The pouch 26 can be separated at any time from the container 18 without putting at risk the sterility of the sample or the component within the container 18.

The illustrated embodiment describes using the sampling device 14 before and after the storage period. Still, it should be realized that air can be removed from the pouch 26 at any point during the collection, storage, or transfusion process. Similarly, a component sample can be drawn from the container into the air-evacuated pouch 26 at any point during the collection, storage, or transfusion process. The period of time that the sample, once drawn, remains in the pouch 26 before being expelled for analysis must take into account the type of blood component and the storage characteristics of the pouch 26 for that component. For this reason, it is desirable to wait until shortly before the sample is required for analysis to draw the sample into the pouch 26, to thereby minimize the time period that the sample dwells in the pouch 26 and maximize the time period that the blood component remains in the associated storage container.

The illustrated embodiment shows use of the device 14 in association with the bag 18 to draw a PC sample. Still, it should be realized that the device 14 can be integrally attached to any bag of a blood processing system to collect samples of any desired component, such as white blood cells, stem cells, red blood cells, granulocytes, and the like. Even when bags of a multiple bag system are separated apart for separate handling and storage, the device 14 remains integrally attach to its associated bag to allow sampling of each individual blood component when desired.

The use of the sampling device 14 requires no special ancillary tools, like tube strippers or syringes. All that is require is squeezing the pouch 26 in coordination with the in-line clamp 38 to obtain a sample under low flow conditions, with no danger of activating or damaging the blood component being sampled.

Furthermore, the interior volume of the pouch 26 fixes the volume of the sample. Thus, consistent size samples of consistent quality can be obtained by different users. The consistency and simplicity of operation remove variances caused by human error and different handling techniques.

Various features of the invention are set forth in the following claims.

We claim:

1. A method of collecting a blood sample comprising the steps of collecting blood in a container, opening communication between the container and an external sample pouch through intermediate tubing, the external sample pouch comprising pouch walls made of a material having resilience to normally maintain the pouch walls in a spaced apart condition containing residual air, with communication open through the intermediate tubing, applying an external squeezing force to move the pouch walls together against the resilience of the material into an essentially collapsed condition and thereby displace the residual air from the sample pouch through the intermediate tubing into the container, closing the intermediate tubing to close communication between the container and the external sample pouch and retain the sample pouch in the essentially collapsed condition against the resilience of the material, with the intermediate tubing closed, orienting the sample pouch in the essentially collapsed condition to receive blood from the container, and with the sample pouch oriented in the essentially collapsed condition to receive blood from the container, opening the intermediate tubing to open communication between the container and the sample pouch through the intermediate tubing, the pouch walls returning, when the intermediate tubing is opened, from the essentially collapsed condition to the spaced apart condition solely in response to the resilience of the material to create a vacuum in the intermediate tubing that draws by suction a sample of the blood from the container into the sample pouch.

2. A method according to claim 1 and further including, after drawing the sample of blood into the sample pouch, the step of closing the intermediate tubing to retain the sample of blood in the sample pouch.

3. A method according to claim 2 and further including, after retaining the sample of blood in the sample pouch, the step of separating from the container the sample pouch and the retained sample of blood.

4. A method according to claim 3 and further including, after separating from the container the sample pouch and retained sample of blood, the step of conveying the retained sample of blood from the sample pouch into a sample vessel.

5. A method according to claim 4 and further including, after separating from the container the sample pouch and retained sample of blood, the step of applying an external squeezing force to the sample pouch to convey the retained sample of blood from the sample pouch into a sample vessel.

* * * * *